US00PP17206P2

(12) United States Plant Patent
Bradford

(10) Patent No.: US PP17,206 P2
(45) Date of Patent: Nov. 14, 2006

(54) NECTARINE TREE NAMED 'PACIFIC SWEET'

(50) Latin Name: *Prunus persica*
Varietal Denomination: PACIFIC SWEET

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 23 days.

(21) Appl. No.: 11/311,175

(22) Filed: Dec. 20, 2005

(51) Int. Cl.
*A01H 5/00* (2006.01)

(52) U.S. Cl. ..... Plt./190
(58) Field of Classification Search ..... Plt./190
See application file for complete search history.

(56) References Cited

U.S. PATENT DOCUMENTS

PP7,507 P 4/1991 Bradford
PP9,963 P 7/1997 Bradford

*Primary Examiner*—Kent Bell
*Assistant Examiner*—Annette H Para

(57) ABSTRACT

The present invention relates to a nectarine tree, *Prunus persica,* and more particularly to a new and distinct variety broadly characterized by a large size, vigorous, hardy, self-fertile, productive and regular bearing tree that requires about 500 chilling hours. The fruit matures under the ecological conditions described in the latter half of June, with first picking on Jun. 19, 2005. The fruit is uniformly large in size, sub-acidic and sweet in flavor, nearly globose in shape, clingstone in type, firm in texture, yellow in flesh color, and full dark red in skin color. The present variety resulted as a second generation cross of 'Spring Bright' (U.S. Plant Pat. No. 7,507) nectarine by an unnamed white flesh nectarine (unpatented).

1 Drawing Sheet

Botanical classification: *Prunus persica.*

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'PACIFIC SWEET'.

The present variety was planted in 1998 as an open pollinated seed of an unnamed white flesh nectarine (unpatented) tree, grown as a seedling on its own root in my greenhouse, and transplanted to a cultivated area of my experimental orchard at Bradford Farms near Le Grand, Calif. in Merced County (San Joaquin Valley). This unnamed seed parent was a first generation gross of 'Spring Bright' (U.S. Plant Pat. No. 7,507) nectarine by another unnamed white flesh nectarine (unpatented). Subsequent to origination of the present variety of peach tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed grandparent, 'Spring Bright' (U.S. Plant Pat. No. 7,507) nectarine, by producing nectarines that are very firm in texture, yellow in flesh color, and full red in skin color, but is distinguished therefrom and by being larger in size, sub-acidic instead of acidic in flavor, and maturing about five days later.

The present variety is most similar to 'Ruby Sweet' (U.S. Plant Pat. No. 9,963) nectarine, by producing nectarines that are very firm in texture, yellow in flesh color, full red in skin color, and sub-acidic in flavor, but is distinguished therefrom by requiring less chilling hours and by producing fruit that is much larger in size.

SUMMARY OF VARIETY

In summary, the present variety is characterized by a large size, vigorous, hardy, self-fertile, productive and regular bearing tree that requires about 500 chilling hours. The fruit matures under the ecological conditions described in the latter half of June, with first picking on Jun. 19, 2005. The fruit is uniformly large in size, sub-acidic and sweet in flavor, nearly globose in shape, clingstone in type, firm in texture, yellow in flesh color, and full dark red in skin color.

DRAWING

The accompanying photograph exhibits four whole fruits positioned to display the characteristics of the skin color and form, one fruit divided transversely to the suture plane to reveal the flesh and stone, a tip shoot, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jun. 22, 2005, on the original tree during its seventh growing season. All major color code designations are by reference to the Inter-Society Color Council, National Bureau of Standards. Common color names are also used occasionally.

Tree

Size: Large, reaching a height of 14' [4.27 m.] and a spread of 10' [3.05 m.] after seven growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and open.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 500 hours.

Trunk:

*Size.*—Medium, with a maximum diameter of 4¼" [108 mm.] after the seventh growing season.

*Texture.*—Somewhat shaggy.

*Bark color.*—A Grayish brown [61. gy.Br] and Moderate brown [58. m.Br.] variegation with Strong yellowish brown [74. s.yBr] crevices present.

*Lenticels.*—Approximate Number Per Square Inch: 9. Color: Dark orange yellow [72. d.OY]. Typical Size: ⅛" [3.2 mm.] to ⅜" [9.5 mm.]. Shape: Eye-shaped to elongated.

Branches:

*Size.*—Diameter of limb is 2⅞" [73 mm.] measured 12" above the crotch, 1¾" [44.5 mm.] measured 12" above the secondary fork.

*Texture.*—Smooth on 1st year wood, increasing roughness with age.

*Color.*—1st Year Wood Topside: Grayish red [19. gy.R]. 1st Year Wood Underside: Strong yellow green [117. s.YG]. Older Wood: Dark yellowish brown [78. d.yBr].

*Lenticels.*—Approximate Number Per Square Inch: 50. Color: Light yellowish brown [76. l.yBr]. Typical size: 1/32" [0.8 mm.] to 3/16" [4.8 mm.]. Shape: Eye-shaped to elongated.

Leaves:

*Size.*—Medium. Average Length: 5¼" [133 mm.]. Average width: 1⅝" [41 mm.].

*Arrangement.*—Alternate.

*Thickness.*—Medium.

*Form.*—Elliptical.

*Apex.*—Acuminate.

*Base.*—Acute, with an average base angle of 80 degrees.

*Surface.*—Smooth.

*Color.*—Dorsal Surface: Moderate olive green [125. m.OlG]. Ventral Surface: Deep yellow green [118. deep YG].

*Margin.*—Finely serrate.

*Venation.*—Pinnately net veined.

*Petiole.*—Average Length: ½" [12.7 mm.]. Average Thickness: 1/16" [1.6 mm.]. Color: Strong yellow green [117. s.YG].

*Stipules.*—Number: 2 per leaf, up to 6 per growing tip. Average Length: ⅜" [9.5 mm.]. Color: Brilliant yellow green [116. brill.YG] turning Moderate reddish brown [43. m.rBr] with maturity.

*Glands.*—Number: 2 to 6. Position: Both alternately and oppositely positioned on both the petiole and base of blade. Size: Medium. Form: Appear to be globose when young, but take on a reniform shape with maturity. Color: Strong yellow green [117. s.YG] on younger leaves turning Moderate reddish brown [43. m.rBr] in the center with maturity.

*Leaf buds.*—Medium in size, pointed.

Flower buds:

*Hardiness.*—Hardy, with respect to central California winters.

*Diameter.*—Typically 5/16" [7.9 mm.] 1 week before bloom.

*Length.*—Typically ½" [12.7 mm.] 1 week before bloom.

*Form.*—Not appressed.

*Surface.*—Pubescent.

*Color.*—Deep purplish pink [248. deep pPk].

Flowers: Perfect, complete, perigynous, usually a single pistil, typically thirty or more stamens, five sepals and petal locations alternately positioned.

*Type.*—Showy, large.

*Average flower diameter.*—2" [50.8 mm.].

*Number of petals.*—Usually five, no double blossoms observed.

*Petal shape.*—Circular.

*Petal margin.*—Mostly smooth.

*Average petal diameter.*—13/16" [20.6 mm.].

*Average petal length.*—13/16" [20.6 mm.].

*Petal apex.*—Rounded.

*Petal base.*—Irregularly rounded.

*Petal color.*—Pale pink [7. p.Pk] toward the apex, Light purplish pink [249. l.pPk] toward the base.

*Anther color.*—Deep reddish orange [36. deep.rO] over Light orange yellow [70. l.OY] centers at bloom onset.

*Stigma color.*—Light greenish yellow [101. l.gY].

*Sepal color.*—Dark purplish red [259. d.pR].

*Sepal length.*—¼" [6 mm.].

*Sepal width.*—3/16" [5 mm.].

*Average pistil length.*¾" [19.1 mm.].

*Average stamen length.*—11/16" [17.5 mm.].

*Fragrance.*—Moderate.

*Blooming period.*—Somewhat early compared with other varieties.

*Onset of bloom.*—One percent on Feb. 17, 2005.

*Date of full bloom.*—Feb. 25, 2005.

*Duration of bloom.*—One to two weeks, dependent on ambient temperature.

*Number per cluster.*—1 to 3 with single flowers most common.

FRUIT

Maturity when described: Firm ripe, Jun. 22, 2005.

Date of first picking: Jun. 19, 2005.

Date of last picking: Jun. 28, 2005.

Size: Uniform, large.

*Average diameter axially.*—3" [76 mm.].

*Average diameter across cheek plane.*—2¾" [70 mm.].

*Average diameter across suture plane.*—3⅛" [79 mm.].

*Typical weight.*—8.6 ounces [244 grams].

Form: Uniform, slightly asymmetrical, globose to slightly oblong.

*Longitudinal section form.*—Oval.

*Axial view form.*—Round with a characteristic hump showing on one side of the suture.

Suture: A shallow groove extending from the stem to just beyond the apex with a slight depression just beyond the pistil point, sharper near the apex and base.

Ventral surface: Rounded, lipped throughout on both sides.

Lips: Larger on one side, fairly equal near the apex.

Cavity: Flaring, circular, slightly elongated in the suture plane, suture showing on one side, Vivid yellow [82. v.Y] stem markings typical.

*Depth.*—7/16 [11.1 mm.].

*Breadth.*—1¼" [31.8 mm.].

Base: Somewhat truncate, cordate if viewed parallel to the suture.

Apex: Rounded.

Pistil point: Mostly apical, short, 1/32" [0.8 mm.] typical length.

Stem: Medium.

*Average length.*—⅜" [9.5 mm.].

*Average width.*—3/16" [4.8 mm.].

Skin:

*Thickness.*—Medium.

*Surface.*—Smooth.

*Tenacity.*—Tenacious to flesh.

*Astringency.*—Nonastringent.

*Tendency to crack.*—None observed.

*Color.*—Very deep red [14. v.deep R] over a Deep red [13. deep R] background with Pale yellow [89. p.Y] freckling toward the apex.

Flesh:

*Color.*—Light yellow [86. l.Y] from the stone to skin with the slightest Moderate red [15. m.R] flecking near the skin.

*Surface of pit cavity.*—Light yellow [86. l.Y] fibers breaking when twisted from the stone.

*Amygdalin.*—Slight.

*Juice.*—Moderate.

*Texture.*—Firm, crisp.

*Fibers.*—Abundant, fine, tender.

*Ripens.*—Slightly earlier toward the apex.

*Flavor.*—Subacid and sweet, typically 16 to 18 brix.

*Aroma.*—Slight.

*Eating quality.*—Good.

STONE

Type: Clingstone.

Form: Oval.

Hilum: Narrow, oval.

Base: Straight.

Apex: Acuminate, with an average tip length of 1/16" [1.6 mm.] and an average angle of 45 degrees.

Sides: Mostly equal.

Surface: Regularly furrowed throughout, ridged near the apex and pitted from base to above center.

Ridges: Jagged.

External color of stone: Dark orange yellow [72. d.OY] when freshly removed.

Pit wall color when cracked: Moderate yellow [87. m.Y] when freshly removed.

Cavity surface color: Strong yellow [84. s.Y] with Moderate yellowish brown [77. m.yBr] specking throughout.

Average pit wall thickness: ¼" [6.4 mm.].

Average width: 15/16" [23.8 mm.].

Average length: 1⅝" [41.3 mm.].

Average breadth: ⅝" [15.9 mm.].

Tendency to split: Slight.

Kernel:

*Form.*—Oval.

*Skin color.*—Brilliant yellow [83. brill.Y] when freshly removed.

*Pellicle color.*—Moderate yellow [87. m.Y].

*Vein color.*—Vivid yellow [82. v.Y].

*Taste.*—Extremely bitter.

*Viable.*—Yes.

*Average width.*—½" [12.7 mm.].

*Average length.*—13/16" [20.6 mm.].

*Amygdalin.*—Abundant.

USE

Market: Fresh market and long distance shipping.

Keeping quality: Good. Fruit quality observed to remain in good condition after 21 days in standard cold room at 36° Fahrenheit [2° Celsius].

Shipping quality: Good.

Resistance to insects: No unusual susceptibilities noted.

Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Ruby Sweet' (U.S. Plant Pat. No. 9,963) nectarine, by producing nectarines that are very firm in texture, yellow in flesh color, full red in skin color, and sub-acidic in flavor, but is distinguished therefrom by requiring less chilling hours and by producing fruit that is much larger in size.

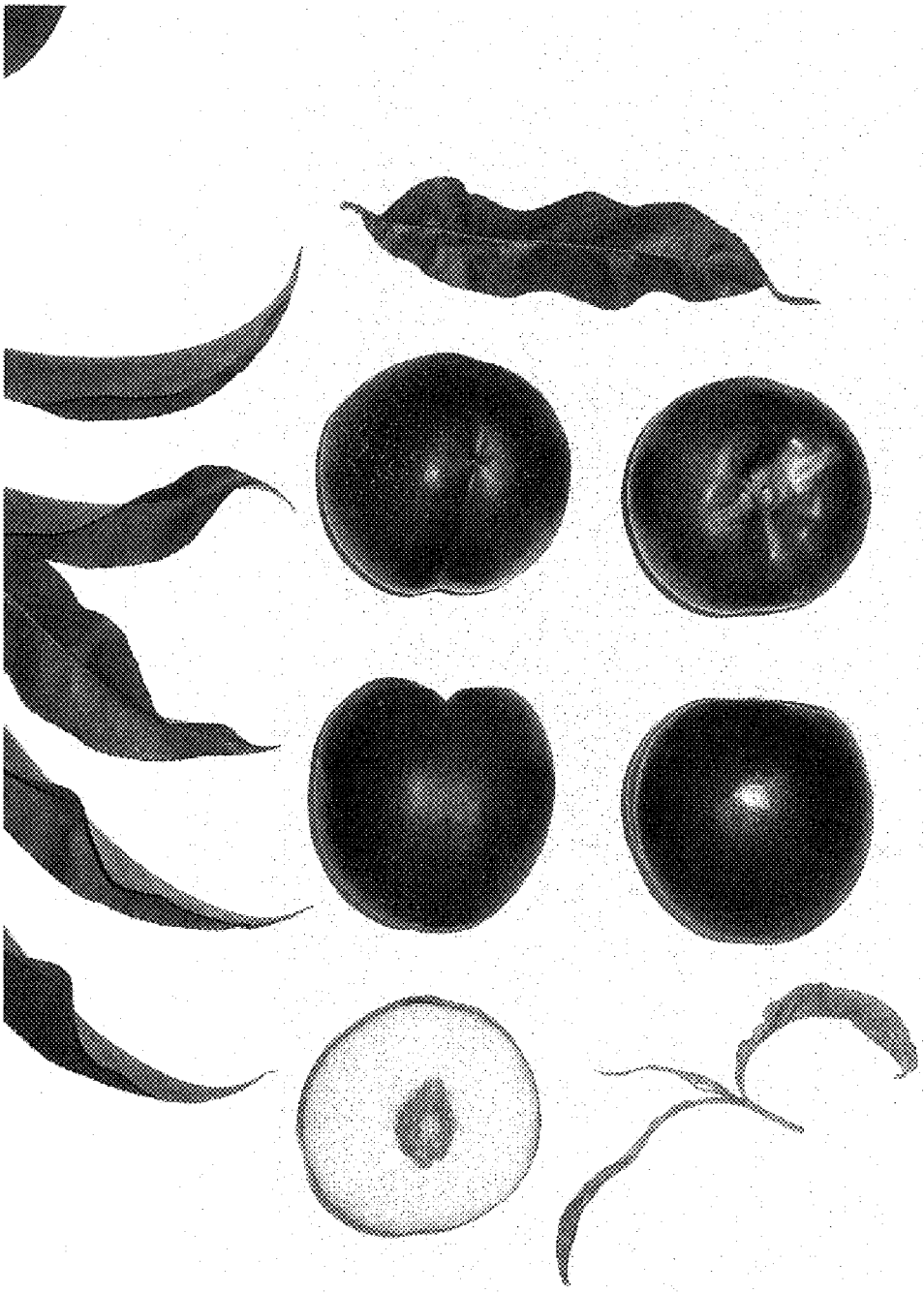

* * * * *